(12) United States Patent
Greeley et al.

(10) Patent No.: US 12,023,082 B2
(45) Date of Patent: Jul. 2, 2024

(54) HEMOSTATIC THERMAL SEALER

(71) Applicant: MEDTRONIC ADVANCED ENERGY, LLC, Minneapolis, MN (US)

(72) Inventors: Roger D. Greeley, Minneapolis, MN (US); Mark Guirguis, Minneapolis, MN (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 720 days.

(21) Appl. No.: 16/053,161

(22) Filed: Aug. 2, 2018

(65) Prior Publication Data

US 2019/0105095 A1 Apr. 11, 2019

Related U.S. Application Data

(60) Provisional application No. 62/568,953, filed on Oct. 6, 2017.

(51) Int. Cl.
| | | |
|---|---|---|
| *A61B 18/08* | (2006.01) | |
| *A61B 18/10* | (2006.01) | |
| *A61B 17/00* | (2006.01) | |
| *A61B 18/00* | (2006.01) | |

(52) U.S. Cl.
CPC ............ *A61B 18/082* (2013.01); *A61B 18/10* (2013.01); *A61B 2017/00853* (2013.01); *A61B 2018/00083* (2013.01); *A61B 2018/00101* (2013.01); *A61B 2018/00107* (2013.01); *A61B 2018/00142* (2013.01); *A61B 2018/0063* (2013.01); *A61B 2018/00636* (2013.01); *A61B 2018/00642* (2013.01); *A61B 2018/00714* (2013.01); *A61B 2018/00791* (2013.01); *A61B 2018/00922* (2013.01); *A61B 2018/087* (2013.01)

(58) Field of Classification Search
CPC ....... A61B 18/04; A61B 18/08; A61B 18/082; A61B 18/085; A61B 18/10; A61B 2018/087; A61B 2018/0063; A61B 2018/00922
USPC ............... 606/27–31, 40, 49; 607/96, 98, 99
See application file for complete search history.

(56) References Cited

U.S. PATENT DOCUMENTS

| | | |
|---|---|---|
| 2,888,928 A | 4/1957 | Seiger |
| 3,223,088 A | 12/1965 | Barber et al. |
| 3,682,130 A | 8/1972 | Jeffers |
| 3,750,650 A | 8/1973 | Ruttgers |
| 3,955,284 A | 5/1976 | Balson |
| 4,014,342 A | 3/1977 | Staub et al. |
| 4,195,637 A | 4/1980 | Gruntzig et al. |
| 4,207,897 A | 6/1980 | Loyd et al. |
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |
| 4,278,090 A | 7/1981 | Van Gerven |
| 4,321,931 A | 3/1982 | Hon |
| 4,342,218 A | 8/1982 | Fox |

(Continued)

*Primary Examiner* — Thomas A Giuliani
(74) *Attorney, Agent, or Firm* — Husch Blackwell LLP

(57) ABSTRACT

A hemostatic sealer includes a handle having a switch to activate a source of thermal energy and a thermal assembly coupled to the handle. The thermal assembly includes an electrically resistive material disposed on an electrically insulative substrate. The resistive material is coupled to the switch to receive the source of thermal energy.

15 Claims, 5 Drawing Sheets

(56) References Cited

U.S. PATENT DOCUMENTS

| | | | |
|---|---|---|---|
| 4,355,642 A | 10/1982 | Alfemess | |
| 4,377,168 A | 3/1983 | Rzasa et al. | |
| 4,381,007 A | 4/1983 | Doss | |
| 4,519,389 A | 5/1985 | Gudkin et al. | |
| 4,598,698 A | 7/1986 | Siegmund | |
| 4,601,290 A | 7/1986 | Effron et al. | |
| 4,664,110 A | 5/1987 | Schanzlin | |
| 4,671,274 A | 6/1987 | Scrochenko | |
| 4,708,126 A | 11/1987 | Toda et al. | |
| 4,736,749 A | 4/1988 | Lundback | |
| 4,779,611 A | 10/1988 | Grooters et al. | |
| 4,802,475 A | 2/1989 | Weshahy | |
| 4,823,791 A * | 4/1989 | D'Amelio | A61B 18/14 606/50 |
| 4,878,493 A | 11/1989 | Pasternak et al. | |
| 4,919,129 A | 4/1990 | Weber et al. | |
| 4,931,047 A | 6/1990 | Broadwin et al. | |
| 4,932,952 A | 6/1990 | Wojciechowicz, Jr. | |
| 4,943,290 A | 7/1990 | Rexroth et al. | |
| 4,950,232 A | 8/1990 | Ruzicka et al. | |
| 4,985,030 A | 1/1991 | Melzer et al. | |
| 4,998,933 A | 3/1991 | Eggers et al. | |
| 5,112,299 A | 5/1992 | Pascaloff | |
| 5,167,659 A | 12/1992 | Ohtomo et al. | |
| 5,190,541 A | 3/1993 | Abele et al. | |
| 5,195,959 A | 3/1993 | Smith | |
| 5,230,704 A | 7/1993 | Moberg et al. | |
| 5,234,428 A | 8/1993 | Kaufman | |
| 5,254,117 A | 10/1993 | Rigby et al. | |
| 5,275,609 A | 1/1994 | Pingleton et al. | |
| 5,281,215 A | 1/1994 | Midler | |
| 5,309,896 A | 5/1994 | Moll et al. | |
| 5,316,000 A | 5/1994 | Chapelon et al. | |
| 5,317,878 A | 6/1994 | Bradshaw et al. | |
| 5,318,525 A | 6/1994 | West et al. | |
| 5,322,520 A | 6/1994 | Milder | |
| 5,323,781 A | 6/1994 | Ideker et al. | |
| 5,324,255 A | 6/1994 | Passafaro et al. | |
| 5,324,284 A | 6/1994 | Imran | |
| 5,324,286 A | 6/1994 | Fowle | |
| 5,330,521 A | 7/1994 | Cohen | |
| 5,334,181 A | 8/1994 | Rubinsky et al. | |
| 5,334,193 A | 8/1994 | Nardella | |
| 5,336,220 A | 8/1994 | Ryan et al. | |
| 5,348,554 A | 9/1994 | Imran et al. | |
| 5,352,222 A | 10/1994 | Rydell et al. | |
| 5,353,783 A | 10/1994 | Nakao et al. | |
| 5,354,258 A | 10/1994 | Dory | |
| 5,361,752 A | 11/1994 | Moll et al. | |
| 5,376,078 A | 12/1994 | Dinger et al. | |
| 5,383,874 A | 1/1995 | Jackson et al. | |
| 5,385,148 A | 1/1995 | Lesh et al. | |
| 5,395,312 A | 3/1995 | Desai | |
| 5,396,887 A | 3/1995 | Imran | |
| 5,397,304 A | 3/1995 | Truckai | |
| 5,400,770 A | 3/1995 | Nakao et al. | |
| 5,400,783 A | 3/1995 | Pomeranz et al. | |
| 5,401,272 A | 3/1995 | Perkins | |
| 5,403,309 A | 4/1995 | Coleman et al. | |
| 5,403,311 A | 4/1995 | Abele et al. | |
| 5,405,348 A | 4/1995 | Anspach et al. | |
| 5,405,376 A | 4/1995 | Mulier et al. | |
| 5,409,483 A | 4/1995 | Campbell et al. | |
| 5,413,556 A | 5/1995 | Whittingham | |
| 5,417,709 A | 5/1995 | Slater | |
| 5,423,807 A | 6/1995 | Mlilder | |
| 5,423,811 A | 6/1995 | Imran et al. | |
| 5,427,119 A | 6/1995 | Swartz et al. | |
| 5,431,168 A | 7/1995 | Webster, Jr. | |
| 5,431,649 A | 7/1995 | Mulier et al. | |
| 5,433,708 A | 7/1995 | Nichols et al. | |
| 5,435,308 A | 7/1995 | Gallup et al. | |
| 5,437,651 A | 8/1995 | Todd et al. | |
| 5,441,503 A | 8/1995 | Considine et al. | |
| 5,443,463 A | 8/1995 | Stem et al. | |
| 5,443,470 A | 8/1995 | Stem et al. | |
| 5,445,638 A | 8/1995 | Rydell et al. | |
| 5,450,843 A | 9/1995 | Moll et al. | |
| 5,452,582 A | 9/1995 | Longsworth | |
| 5,452,733 A | 9/1995 | Sterman et al. | |
| 5,460,629 A | 10/1995 | Shlain et al. | |
| 5,462,545 A | 10/1995 | Wang et al. | |
| 5,465,717 A | 11/1995 | Imran et al. | |
| 5,469,853 A | 11/1995 | Law et al. | |
| 5,472,876 A | 12/1995 | Fahy | |
| 5,478,309 A | 12/1995 | Sweezer et al. | |
| 5,478,330 A | 12/1995 | Imran et al. | |
| 5,486,193 A | 1/1996 | Bourne et al. | |
| 5,487,385 A | 1/1996 | Avitall | |
| 5,487,757 A | 1/1996 | Truckai et al. | |
| 5,490,819 A | 2/1996 | Nicholas et al. | |
| 5,492,527 A | 2/1996 | Glowa et al. | |
| 5,496,271 A | 3/1996 | Burton et al. | |
| 5,496,312 A | 3/1996 | Klicek | |
| 5,497,774 A | 3/1996 | Swartz et al. | |
| 5,498,248 A | 3/1996 | Milder | |
| 5,500,012 A | 3/1996 | Brucker et al. | |
| 5,505,500 A | 4/1996 | Webb et al. | |
| 5,505,730 A | 4/1996 | Edwards | |
| 5,516,505 A | 5/1996 | McDow | |
| 5,520,682 A | 5/1996 | Baust et al. | |
| 5,522,870 A | 6/1996 | Ben-Zion | |
| 5,536,267 A | 7/1996 | Edwards et al. | |
| 5,540,562 A | 7/1996 | Giter | |
| 5,540,708 A | 7/1996 | Lim et al. | |
| 5,542,196 A | 8/1996 | Hirsch et al. | |
| 5,542,945 A | 8/1996 | Fritzsch | |
| 5,545,195 A | 8/1996 | Lennox et al. | |
| 5,545,200 A | 8/1996 | West et al. | |
| 5,549,661 A | 8/1996 | Kordis et al. | |
| 5,555,883 A | 9/1996 | Avitall | |
| 5,556,397 A | 9/1996 | Long et al. | |
| 5,558,671 A | 9/1996 | Yates | |
| 5,560,362 A | 10/1996 | Silwa, Jr. et al. | |
| 5,560,373 A | 10/1996 | DeSantis | |
| 5,562,702 A | 10/1996 | Huitema et al. | |
| 5,562,720 A | 10/1996 | Stem et al. | |
| 5,569,241 A | 10/1996 | Edwards | |
| 5,569,243 A | 10/1996 | Kortenbach et al. | |
| 5,569,254 A | 10/1996 | Carlson et al. | |
| 5,571,088 A | 11/1996 | Lennox et al. | |
| 5,571,215 A | 11/1996 | Sterman et al. | |
| 5,573,424 A | 11/1996 | Poppe | |
| 5,573,532 A | 11/1996 | Chang et al. | |
| 5,575,766 A | 11/1996 | Swartz et al. | |
| 5,575,788 A | 11/1996 | Baker et al. | |
| 5,575,810 A | 11/1996 | Swanson et al. | |
| 5,578,007 A | 11/1996 | Imran | |
| 5,582,609 A | 12/1996 | Swanson et al. | |
| 5,588,432 A | 12/1996 | Crowley | |
| 5,590,657 A | 1/1997 | Cain et al. | |
| 5,595,183 A | 1/1997 | Swanson et al. | |
| 5,599,346 A | 2/1997 | Edwards et al. | |
| 5,605,539 A | 2/1997 | Buelna et al. | |
| 5,607,462 A | 3/1997 | Imran | |
| 5,609,573 A | 3/1997 | Sandock | |
| 5,617,854 A | 4/1997 | Munsif | |
| 5,620,415 A | 4/1997 | Lucey et al. | |
| 5,620,447 A | 4/1997 | Smith et al. | |
| 5,630,837 A | 5/1997 | Crowley | |
| 5,643,197 A | 7/1997 | Brucker et al. | |
| 5,647,869 A | 7/1997 | Goble et al. | |
| 5,656,029 A | 8/1997 | Imran et al. | |
| 5,658,278 A | 8/1997 | Imran et al. | |
| 5,637,090 A | 9/1997 | McGee et al. | |
| 5,671,747 A | 9/1997 | Connor | |
| 5,673,695 A | 10/1997 | McGee et al. | |
| 5,676,662 A | 10/1997 | Fleischhacker et al. | |
| 5,676,692 A | 10/1997 | Sanghvi et al. | |
| 5,676,693 A | 10/1997 | Lafontaine | |
| 5,678,550 A | 10/1997 | Bassen et al. | |
| 5,680,860 A | 10/1997 | Imran | |
| 5,681,278 A | 10/1997 | Igo et al. | |
| 5,681,294 A | 10/1997 | Osborne et al. | |

(56) References Cited

U.S. PATENT DOCUMENTS

| | | |
|---|---|---|
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,702,390 A | 12/1997 | Austin et al. |
| 5,712,543 A | 1/1998 | Sjostrom |
| 5,713,942 A | 2/1998 | Stem |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Lanard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,743,903 A | 4/1998 | Stem et al. |
| 5,755,760 A | 5/1998 | Maguire et al. |
| 5,766,167 A | 6/1998 | Eggers et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,792,167 A | 8/1998 | Kablik et al. |
| 5,797,905 A | 8/1998 | Fleischman et al. |
| 5,797,960 A | 8/1998 | Stevens et al. |
| 5,735,290 A | 9/1998 | Nelson et al. |
| 5,800,428 A | 9/1998 | Nelson et al. |
| 5,800,482 A | 9/1998 | Pomeranz et al. |
| 5,810,764 A | 9/1998 | Eggers et al. |
| 5,810,802 A | 9/1998 | Panescu et al. |
| 5,810,809 A | 9/1998 | Rydell |
| 5,814,044 A | 9/1998 | Hooven |
| 5,827,216 A | 10/1998 | Igo et al. |
| 5,836,947 A | 11/1998 | Fleischman et al. |
| 5,840,030 A | 11/1998 | Ferek-Petric et al. |
| 5,843,021 A | 12/1998 | Edwards et al. |
| 5,843,152 A | 12/1998 | Tu et al. |
| 5,844,349 A | 12/1998 | Oakley et al. |
| 5,846,187 A | 12/1998 | Wells et al. |
| 5,846,191 A | 12/1998 | Wells et al. |
| 5,849,023 A | 12/1998 | Mericle |
| 5,849,028 A | 12/1998 | Chen |
| 5,861,021 A | 1/1999 | Thome et al. |
| 5,871,523 A | 2/1999 | Fleischman et al. |
| 5,871,525 A | 2/1999 | Edwards et al. |
| 5,873,845 A | 2/1999 | Cline et al. |
| 5,873,855 A | 2/1999 | Eggers et al. |
| 5,873,886 A | 2/1999 | Larsen et al. |
| 5,876,399 A | 3/1999 | Chia et al. |
| 5,879,295 A | 3/1999 | Li et al. |
| 5,879,296 A | 3/1999 | Ockuly et al. |
| 5,879,348 A | 3/1999 | Owens et al. |
| 5,881,732 A | 3/1999 | Sung et al. |
| 5,882,346 A | 3/1999 | Pomeranz et al. |
| 5,885,278 A | 3/1999 | Fleischman |
| 5,891,142 A | 4/1999 | Eggers et al. |
| 5,893,848 A | 4/1999 | Negus et al. |
| 5,895,355 A | 4/1999 | Schaer |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,899,915 A | 5/1999 | Saadat |
| 5,902,289 A | 5/1999 | Swartz et al. |
| 5,904,681 A | 5/1999 | West, Jr. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,913,854 A | 6/1999 | Maguire et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,925,045 A | 7/1999 | Reimels et al. |
| 5,927,284 A | 7/1999 | Borst et al. |
| 5,931,810 A | 8/1999 | Grabek |
| 5,931,848 A | 8/1999 | Saadat |
| 5,935,123 A | 8/1999 | Edwards et al. |
| 5,944,715 A | 8/1999 | Goble et al. |
| 5,928,191 A | 9/1999 | Houser et al. |
| 5,954,661 A | 9/1999 | Greenspon et al. |
| 5,975,919 A | 9/1999 | Laufer |
| 5,971,980 A | 10/1999 | Sherman |
| 5,971,983 A | 10/1999 | Lesh |
| 5,980,516 A | 11/1999 | Mulier et al. |
| 5,989,248 A | 11/1999 | Tu et al. |
| 5,993,412 A | 11/1999 | Deily et al. |
| 5,993,447 A | 11/1999 | Blewett et al. |
| 6,004,316 A | 12/1999 | Laufer |
| 6,004,319 A | 12/1999 | Goble et al. |
| 6,007,499 A | 12/1999 | Martin |
| 6,010,500 A | 1/2000 | Sherman et al. |
| 6,012,457 A | 1/2000 | Lesh |
| 6,015,391 A | 1/2000 | Rishton et al. |
| 6,016,811 A | 1/2000 | Knopp et al. |
| 6,018,676 A | 1/2000 | Davis et al. |
| 6,019,757 A | 2/2000 | Scheldrup |
| 6,024,733 A | 2/2000 | Eggers et al. |
| 6,030,381 A | 2/2000 | Jones et al. |
| 6,036,687 A | 3/2000 | Laufer et al. |
| 6,042,556 A | 3/2000 | Beach et al. |
| 6,042,593 A | 3/2000 | Storz et al. |
| 6,048,333 A | 4/2000 | Lennox et al. |
| 6,053,923 A | 4/2000 | Veca et al. |
| 6,056,744 A | 5/2000 | Edwards |
| 6,056,745 A | 5/2000 | Panescu et al. |
| 6,056,746 A | 5/2000 | Goble |
| 6,056,747 A | 5/2000 | Saadat et al. |
| 6,066,139 A | 5/2000 | Ryan et al. |
| 6,068,653 A | 5/2000 | LaFontaine |
| 6,083,237 A | 7/2000 | Huitema et al. |
| 6,086,585 A | 7/2000 | Hovda et al. |
| 6,113,596 A | 9/2000 | Hooven et al. |
| 6,117,101 A | 9/2000 | Diederich et al. |
| 6,120,496 A | 9/2000 | Whayne et al. |
| 6,141,576 A | 10/2000 | Littmann et al. |
| 6,142,993 A | 11/2000 | Whayne et al. |
| 6,142,994 A | 11/2000 | Swanson et al. |
| 6,149,620 A | 11/2000 | Baker et al. |
| 6,152,920 A | 11/2000 | Thompson et al. |
| 6,161,543 A | 12/2000 | Cox et al. |
| 6,165,174 A | 12/2000 | Jacobs et al. |
| 6,190,384 B1 | 2/2001 | Ouchi |
| 6,193,716 B1 | 2/2001 | Shannon, Jr. |
| 6,210,406 B1 | 4/2001 | Webster |
| 6,210,410 B1 | 4/2001 | Farin et al. |
| 6,210,411 B1 | 4/2001 | Hofmann et al. |
| 6,212,426 B1 | 4/2001 | Swanson |
| 6,224,592 B1 | 5/2001 | Eggers et al. |
| 6,231,518 B1 | 5/2001 | Grabek et al. |
| 6,231,591 B1 | 5/2001 | Desai |
| 6,235,020 B1 | 5/2001 | Cheng et al. |
| 6,237,605 B1 | 5/2001 | Vaska et al. |
| 6,238,347 B1 | 5/2001 | Nix et al. |
| 6,238,387 B1 | 5/2001 | Miller, III |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,110 B1 | 6/2001 | Wampler |
| 6,251,128 B1 | 6/2001 | Knopp et al. |

(56) References Cited

U.S. PATENT DOCUMENTS

| | | | |
|---|---|---|---|
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,283,988 B1 | 9/2001 | Laufer et al. |
| 6,283,989 B1 | 9/2001 | Laufer et al. |
| 6,296,638 B1 | 10/2001 | Davison et al. |
| 6,299,633 B1 | 10/2001 | Laufer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,956 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli |
| 6,494,892 B1 | 12/2002 | Ireland et al. |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,517,536 B2 | 2/2003 | Hooven et al. |
| 6,537,248 B2 | 3/2003 | Mulier |
| 6,537,272 B2 | 3/2003 | Hoey |
| 6,558,382 B2 | 5/2003 | Jahns |
| 6,558,385 B1 | 5/2003 | Bloom et al. |
| 6,575,969 B1 | 6/2003 | Rittman, III et al. |
| 6,579,288 B1 | 6/2003 | Swanson et al. |
| 6,585,732 B2 | 7/2003 | Mulier |
| 6,602,248 B1 | 8/2003 | Sharps et al. |
| 6,603,988 B2 | 8/2003 | Dowlatshahi |
| 6,610,055 B1 | 8/2003 | Swanson et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson |
| 6,689,131 B2 | 2/2004 | McClurken |
| 6,702,810 B2 | 3/2004 | McClurken et al. |
| 6,706,038 B2 | 3/2004 | Francischelli |
| 6,706,039 B2 | 3/2004 | Mulier |
| 6,716,211 B2 | 4/2004 | Mulier |
| 6,716,215 B1 | 4/2004 | David et al. |
| 6,736,810 B2 | 5/2004 | Hoey |
| 6,752,816 B2 | 6/2004 | Culp et al. |
| 6,755,827 B2 | 6/2004 | Mulier |
| 6,764,487 B2 | 7/2004 | Mulier |
| 6,766,817 B2 | 7/2004 | da Silva |
| 6,775,575 B2 | 8/2004 | Bommannan et al. |
| 6,776,780 B2 | 8/2004 | Mulier |
| 6,786,906 B1 | 9/2004 | Cobb |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | Bloom et al. |
| 6,960,205 B2 | 11/2005 | Jahns |
| 6,962,589 B2 | 11/2005 | Mulier |
| 6,979,332 B2 | 12/2005 | Adams |
| 7,018,241 B2 | 3/2006 | Caveney et al. |
| 7,048,687 B1 | 5/2006 | Reuss et al. |
| 7,066,586 B2 | 6/2006 | da Silva |
| 7,156,845 B2 | 1/2007 | Mulier et al. |
| 7,166,106 B2 | 1/2007 | Bartel et al. |
| 7,179,255 B2 | 2/2007 | Lettice et al. |
| 7,207,471 B2 | 4/2007 | Heinrich et al. |
| 7,232,440 B2 | 6/2007 | Dumbauld et al. |
| 7,237,990 B2 | 7/2007 | Deng |
| 7,247,155 B2 | 7/2007 | Hoey et al. |
| 7,247,161 B2 | 7/2007 | Johnston et al. |
| 7,261,711 B2 | 8/2007 | Mulier et al. |
| 7,276,074 B2 | 10/2007 | Adams et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,445,436 B2 | 11/2008 | Mittelstein et al. |
| 7,537,595 B2 * | 5/2009 | McClurken ........ A61B 18/1492 606/50 |
| 7,604,635 B2 | 10/2009 | Bloom et al. |
| 7,645,277 B2 | 1/2010 | Bloom et al. |
| 7,651,494 B2 | 1/2010 | Bloom et al. |
| 7,736,361 B2 | 6/2010 | Palanker |
| 7,776,014 B2 | 8/2010 | Visconti et al. |
| 7,815,634 B2 | 10/2010 | Bloom et al. |
| 7,909,820 B2 | 3/2011 | Lipson et al. |
| 7,918,852 B2 | 4/2011 | Tullis et al. |
| 7,942,872 B2 | 5/2011 | Ein-Gal |
| 7,976,544 B2 | 7/2011 | McClurken et al. |
| 7,993,337 B2 | 8/2011 | Lesh |
| 7,997,278 B2 | 8/2011 | Utley et al. |
| 7,998,140 B2 | 8/2011 | McClurken |
| 8,034,071 B2 | 10/2011 | Scribner et al. |
| 8,038,670 B2 | 10/2011 | McClurken |
| 8,048,070 B2 | 11/2011 | O'Brien et al. |
| 8,083,736 B2 | 12/2011 | Bloom et al. |
| 8,109,956 B2 | 2/2012 | Shadeck |
| 8,172,828 B2 | 4/2012 | Chang et al. |
| 8,177,783 B2 | 5/2012 | Davison et al. |
| 8,202,288 B2 | 6/2012 | Adams et al. |
| 8,216,233 B2 | 7/2012 | McClurken et al. |
| 8,323,276 B2 | 12/2012 | Palanker et al. |
| 8,348,946 B2 | 1/2013 | McClurken et al. |
| 8,361,068 B2 | 1/2013 | McClurken |
| 8,388,642 B2 | 3/2013 | Muni et al. |
| 8,414,572 B2 | 4/2013 | Davison et al. |

(56) References Cited

U.S. PATENT DOCUMENTS

| | | |
|---|---|---|
| 8,475,455 B2 | 7/2013 | McClurken et al. |
| 8,562,598 B2 | 10/2013 | Falkenstein et al. |
| 8,568,409 B2 | 10/2013 | O'Brien et al. |
| 8,632,533 B2 | 1/2014 | Greeley et al. |
| 8,882,756 B2 | 11/2014 | Greeley et al. |
| 8,906,012 B2 | 12/2014 | Conley et al. |
| 8,920,417 B2 | 12/2014 | Conley et al. |
| 8,979,842 B2 | 3/2015 | McNall, III et al. |
| 2001/0032002 A1 | 10/2001 | McClurken et al. |
| 2001/0047183 A1 | 11/2001 | Privitera et al. |
| 2002/0038129 A1 | 3/2002 | Peters et al. |
| 2002/0049483 A1 | 4/2002 | Knowlton |
| 2002/0062131 A1 | 5/2002 | Gallo, Sr. |
| 2002/0082643 A1 | 6/2002 | Kammerer et al. |
| 2002/0165541 A1 | 11/2002 | Whitman |
| 2002/0198519 A1 | 12/2002 | Qin et al. |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0097129 A1 | 5/2003 | Davison et al. |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0193151 A1* | 9/2004 | To ................. A61B 18/1492 606/41 |
| 2004/0204679 A1 | 10/2004 | Visconti et al. |
| 2004/0215183 A1 | 10/2004 | Hoey |
| 2004/0220560 A1 | 11/2004 | Briscoe |
| 2004/0236322 A1 | 11/2004 | Mulier |
| 2004/0243163 A1 | 12/2004 | Casiano et al. |
| 2004/0267326 A1 | 12/2004 | Ocel |
| 2005/0010095 A1 | 1/2005 | Stewart et al. |
| 2005/0037672 A1 | 2/2005 | Caveney et al. |
| 2005/0069437 A1 | 3/2005 | Mittelstein et al. |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0171525 A1 | 8/2005 | Rioux et al. |
| 2005/0209564 A1 | 9/2005 | Bonner |
| 2005/0222566 A1 | 10/2005 | Nahahira |
| 2005/0267454 A1 | 12/2005 | Hissong |
| 2005/0277970 A1 | 12/2005 | Norman et al. |
| 2006/0009756 A1 | 1/2006 | Francischelli |
| 2006/0009759 A1 | 1/2006 | Christian |
| 2006/0064085 A1 | 3/2006 | Schechter et al. |
| 2006/0106375 A1 | 5/2006 | Werneth et al. |
| 2006/0149225 A1 | 7/2006 | McClurken |
| 2007/0016185 A1 | 1/2007 | Tullis et al. |
| 2007/0049920 A1 | 3/2007 | Bloom et al. |
| 2007/0049999 A1* | 3/2007 | Esch .................. A61B 18/082 607/96 |
| 2007/0093808 A1 | 4/2007 | Mulier et al. |
| 2007/0112343 A1 | 5/2007 | Mische et al. |
| 2007/0118114 A1 | 5/2007 | Miller et al. |
| 2007/0149965 A1 | 6/2007 | Gallo, Sr. et al. |
| 2007/0208332 A1 | 9/2007 | Mulier et al. |
| 2008/0004656 A1 | 1/2008 | Livneh |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0103494 A1 | 5/2008 | Rioux et al. |
| 2008/0207208 A1 | 8/2008 | Schutz |
| 2008/0208189 A1* | 8/2008 | Van Wyk ............... A61B 18/18 606/41 |
| 2008/0262489 A1 | 10/2008 | Steinke |
| 2009/0222001 A1 | 9/2009 | Greeley et al. |
| 2009/0264879 A1 | 10/2009 | Bloom et al. |
| 2009/0270896 A1 | 10/2009 | Sullivan et al. |
| 2009/0306655 A1 | 12/2009 | Stangenes |
| 2010/0069904 A1 | 3/2010 | Cunningham |
| 2010/0100095 A1 | 4/2010 | Bloom et al. |
| 2010/0160906 A1 | 6/2010 | Jarrard |
| 2010/0168743 A1 | 7/2010 | Stone et al. |
| 2010/0204560 A1 | 8/2010 | Salahieh et al. |
| 2010/0241178 A1 | 9/2010 | Tilson et al. |
| 2010/0298763 A1 | 11/2010 | Adams et al. |
| 2011/0009856 A1 | 1/2011 | Jorgensen et al. |
| 2011/0028965 A1 | 2/2011 | McClurken |
| 2011/0137298 A1 | 6/2011 | Nguyen et al. |
| 2011/0178515 A1 | 7/2011 | Bloom et al. |
| 2011/0196367 A1 | 8/2011 | Gallo |
| 2011/0270250 A1* | 11/2011 | Horner ................. A61B 18/085 606/49 |
| 2011/0295249 A1 | 12/2011 | Bloom et al. |
| 2011/0301578 A1 | 12/2011 | Muniz-Medina et al. |
| 2011/0319889 A1 | 12/2011 | Conley et al. |
| 2012/0004657 A1 | 1/2012 | Conley et al. |
| 2012/0021035 A1 | 2/2012 | Harvey |
| 2012/0071712 A1 | 3/2012 | Manwaring et al. |
| 2012/0095461 A1 | 4/2012 | Herscher et al. |
| 2012/0101496 A1 | 4/2012 | McClurken et al. |
| 2012/0116397 A1 | 5/2012 | Rencher et al. |
| 2012/0143293 A1 | 6/2012 | Mauch et al. |
| 2012/0151165 A1 | 6/2012 | Conley et al. |
| 2012/0157989 A1 | 6/2012 | Stone et al. |
| 2012/0184983 A1 | 7/2012 | Chang et al. |
| 2012/0191084 A1 | 7/2012 | Davison et al. |
| 2012/0191117 A1 | 7/2012 | Palmer et al. |
| 2012/0253343 A1 | 10/2012 | McClurken et al. |
| 2013/0066310 A1 | 3/2013 | Manwaring et al. |
| 2013/0158535 A1 | 6/2013 | Denis et al. |
| 2013/0197502 A1 | 8/2013 | Manwaring et al. |
| 2014/0005667 A1* | 1/2014 | Stulen .................. A61B 18/14 606/45 |
| 2014/0188105 A1 | 7/2014 | Conley et al. |

* cited by examiner

HEMOSTATIC THERMAL SEALER

CROSS REFERENCE TO RELATED APPLICATION

This Non-Provisional Utility application claims benefit to U.S. Provisional Application No. 62/568,953, filed Oct. 6, 2017, titled "HEMOSTATIC SURGICAL SEALER," the entirety of which incorporated herein by reference.

BACKGROUND

This disclosure relates generally to the field of medical devices, systems and methods for use in surgical procedures. More specifically, this disclosure relates to surgical devices, units, systems and methods that can provide for hemostasis or sealing of bodily tissues including bone.

The management and control of intraoperative bleeding can include the techniques of coagulation, hemostasis, or sealing of tissues and are often performed with the aid of electrodes energized from a suitable power source. Typical electrosurgical devices apply an electrical potential difference or signal between an active electrode and a return electrode on a patient's grounded body or between an active electrode and a return electrode on the device to deliver electrical energy to the area where tissue is to be affected. Electrosurgical devices pass electrical energy through tissue between the electrodes to provide coagulation to control bleeding and hemostasis to seal tissue. The electrosurgical devices are usually held by the surgeon and connected to the power source, such as an electrosurgical unit having a power generator, via cabling.

Dry-tip electrosurgical devices can adversely affect tissue and surgical procedures by desiccating or perforating tissue, causing tissue to stick to the electrodes, burning or charring tissue, and generating smoke at the surgical site. More recently, fluid-assisted electrosurgical devices have been developed that use saline to inhibit such undesirable effects as well as to control the temperature of the tissue being treated and to electrically couple the device to the tissue. Fluid-assisted electrosurgical devices have been developed which, when used in conjunction with an electrically conductive fluid such as saline, may be moved along a tissue surface without cutting the tissue to seal tissue to inhibit blood and other fluid loss during surgery.

Fluid-assisted electrosurgical devices apply radiofrequency (RF) electrical energy and electrically conductive fluid to provide for sealing of soft tissues and bone in applications of orthopedics (such as total hip arthroplasty, or THA, and total knee arthroplasty, or TKA), spinal oncology, neurosurgery, thoracic surgery, and cardiac implantable electronic devices as well as others such as general surgery within the human body. The combination of RF energy and the electrically conductive fluid permits the electrosurgical device to operate at approximately 100 degrees Celsius, which is nearly 200 degrees Celsius less than traditional electrosurgical devices. Typically, hemostasis is performed with fluid-assisted devices having electrodes in the bipolar arrangement that are referred to as bipolar sealers. By controlling bleeding, bipolar sealers have been demonstrated to reduce the incidence of hematoma and transfusions, help maintain hemoglobin levels, and reduce surgical time in a number of procedures, and may reduce the use of hemostatic agents.

SUMMARY

This summary is provided to introduce a selection of concepts in a simplified form that are further described below in the Detailed Description.

An aspect of the present disclosure includes a surgical system, method, and surgical devices that can provide the therapeutic analog of traditional electrosurgical hemostatic sealing without dispersing or constantly dispersing fluid such as saline or deionized water at the surgical site. The use of the surgical device as a hemostatic sealer simplifies surgical preparation and procedures as it reduces the use of suction, and can eliminate hot saline at the surgical site. Further, the surgical device provides precise temperature control in various conditions and targeted treatment. The surgical device can be more ergonomic via a lighter attached cable, such as a cable without a saline tube, or a cordless handpiece.

In one aspect, the disclosure is directed to a surgical device configured as a hemostatic sealer. The hemostatic sealer includes a handle having a switch to activate a source of thermal energy and a thermal assembly coupled to the handle. The thermal assembly includes an electrically resistive material disposed on an electrically insulative substrate. The resistive material is coupled to the switch to receive the source of thermal energy.

In another aspect, the disclosure is directed to a surgical device configured as a hemostatic sealer. The surgical device includes a handle having a switch, a shaft extending distally from the handle, and a thermal assembly operably coupled to the shaft. The thermal assembly includes a heating element and an electrically insulative substrate. The substrate provides a shape of the thermal assembly. The heating element includes an electrically resistive material electrically coupled to the switch and disposed on the substrate.

The surgical device includes a thermal assembly that provides even thermal therapy and bleeding management with precise temperature control that will interface with tissue. Activation of the thermal assembly quickly heats a heating element into the temperature range of about 80 degrees Celsius to 110 degrees Celsius, i.e., the known temperature range for good hemostasis, and will quickly reduce heat at deactivation of the thermal assembly to avoid inadvertent thermal damage to tissue, the surgical drape, or other surgical equipment. In one example, the thermal assembly heats to the selected thermal range upon one second of activation and cools to a safe temperature within one second of deactivation.

Precise temperature control is provided with two features. First, the heating assembly includes a heating element formed of a thin electrically resistive material on a thermally insulative and durable substrate. The heating element is coupled to a source of electrical energy, which is not limited to the RF range. In one example, the heating element includes a thin nickel-chrome plating in the range of 0.001 to 0.005 inches thick on a ceramic substrate. Second, the resistance or impedance of the heating element changes with temperature, and the resistance or impedance is monitored with a controller. The controller maintains the target temperature in the thermal assembly via selective operation of the source of electrical energy. In one example, the source of electrical energy and the controller can be included within a handheld surgical device.

The surface of the thermal assembly is smooth and slides along the tissue without saline. In one example, the surface of the thermal assembly includes a lubricious or non-stick coating to improve lubricity.

DETAILED DESCRIPTION

Figure 1:
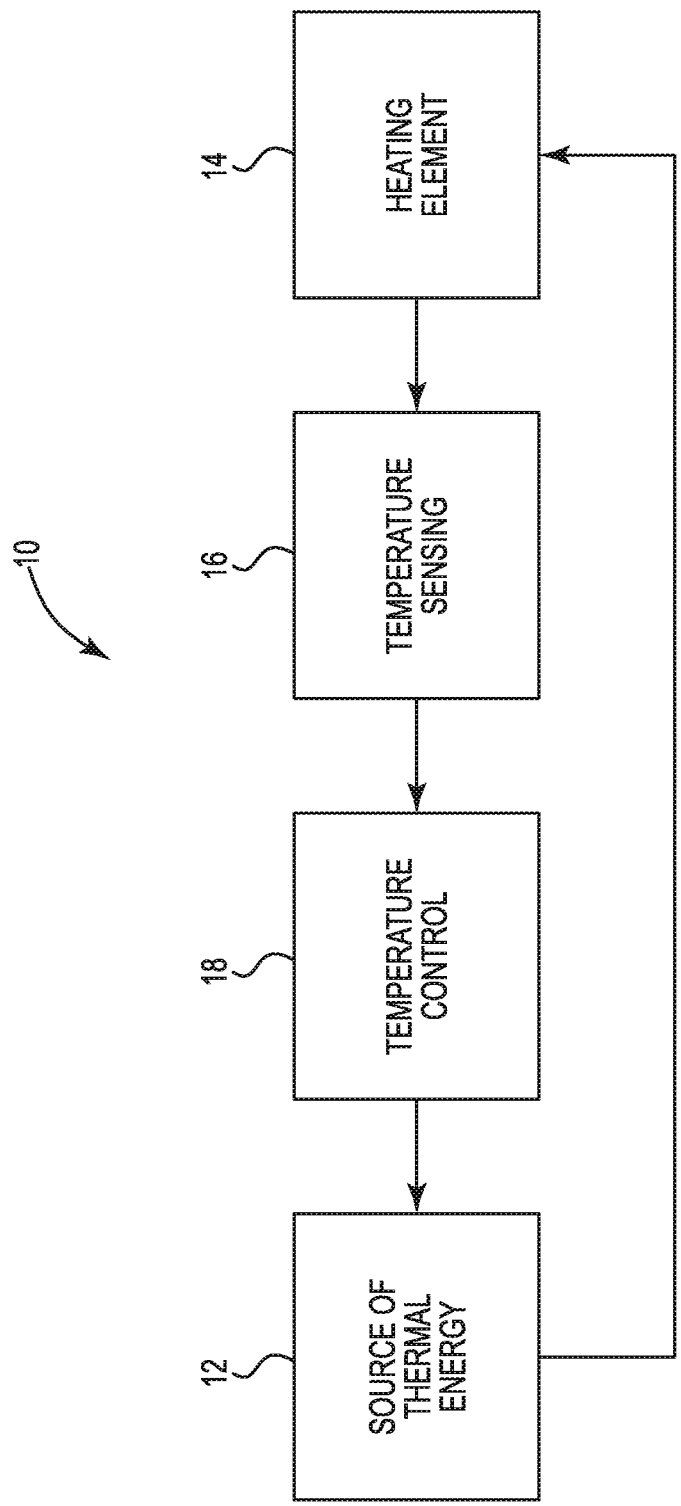
FIG. 1 is a schematic view illustrating a surgical system of the disclosure.

Throughout the description, like reference numerals and letters indicate corresponding structure throughout the several views. Also, any particular features(s) of a particular exemplary embodiment may be equally applied to any other exemplary embodiment(s) of this specification as suitable. That is, features between the various exemplary embodiments described herein are interchangeable as suitable and may not be exclusive. From the specification, it should be clear that the terms "distal" and "proximal" are made in reference to a user of the device.

FIG. 1 illustrates a surgical system 10 that can include a handheld surgical device to deliver thermal energy to provide hemostasis or sealing of body tissues including bone without the use or fluid or without the constant dispersal of fluid. In one example, the system 10 can be included within a handheld surgical device. In still another example, the system 10 can include a selectively dispersed fluid, e.g. a fluid can be dispersed at the discretion of the operator of the system 10 rather than constantly dispersed while the device is activated.

The system 10 includes a source of thermal energy 12 coupled to a heating element 14. In one example, the source of thermal energy 12 includes a source of electrical energy electrically coupled to the heating element 14. The heating element 14 can be configured as part of heating assembly on a distal tip of a surgical device. The heating element 14 can include a resistive material that is configured to rise in temperature when an electrical current is passed through the heating element 14. The source of thermal energy 12 can be selectively activated via a switch to apply the electrical current to the heating element 14. Activation of the thermal assembly quickly heats the heating element 14 into the temperature range of about 80 degrees Celsius to 110 degrees Celsius, such as to a preselected temperature within that range. In one example, the heating element include a low thermal mass or heat capacity so that the heating element 14 heats to the preselected temperature or temperature range upon one second of activation and cools to a safe temperature within one second of deactivation.

The system 10 includes a temperature detection mechanism 16 operably coupled to detect the temperature of the heating element 14. The temperature detection mechanism 16 can directly or inferentially determine temperature of the heating element 14. In one example, the temperature detection mechanism includes a thermocouple. In another example, the resistance or impedance of the heating element 14 changes with temperature, and the resistance or impedance of the heating element 14 is detected with the temperature detection mechanism 16. The temperature detection mechanism 16 is operably coupled to a controller 18 to monitor the temperature of the heating element 14. The controller 18 can include a processor and memory to execute a set of instructions in an application to monitor and control the temperature of the heating element 14 with the source of thermal energy 12. In some examples, the system 10 can include a display or a data output couplable to an external monitor to provide graphical or indications of temperature or other information as determined by the controller 18.

In some examples, the system 10 may provide for a selective application of fluid if desired by a surgeon. Fluid may be provided from a fluid source that can include a bag of fluid through a drip chamber to delivery tubing and to a handheld surgical device. In one example, the fluid includes saline and can include physiologic saline such as sodium chloride (NaCl) 0.9% weight/volume solution. Saline is an electrically conductive fluid, and other suitable electrically conductive fluids can be used. In other examples, the fluid may include a nonconductive fluid, such as deionized water.

Figure 2:
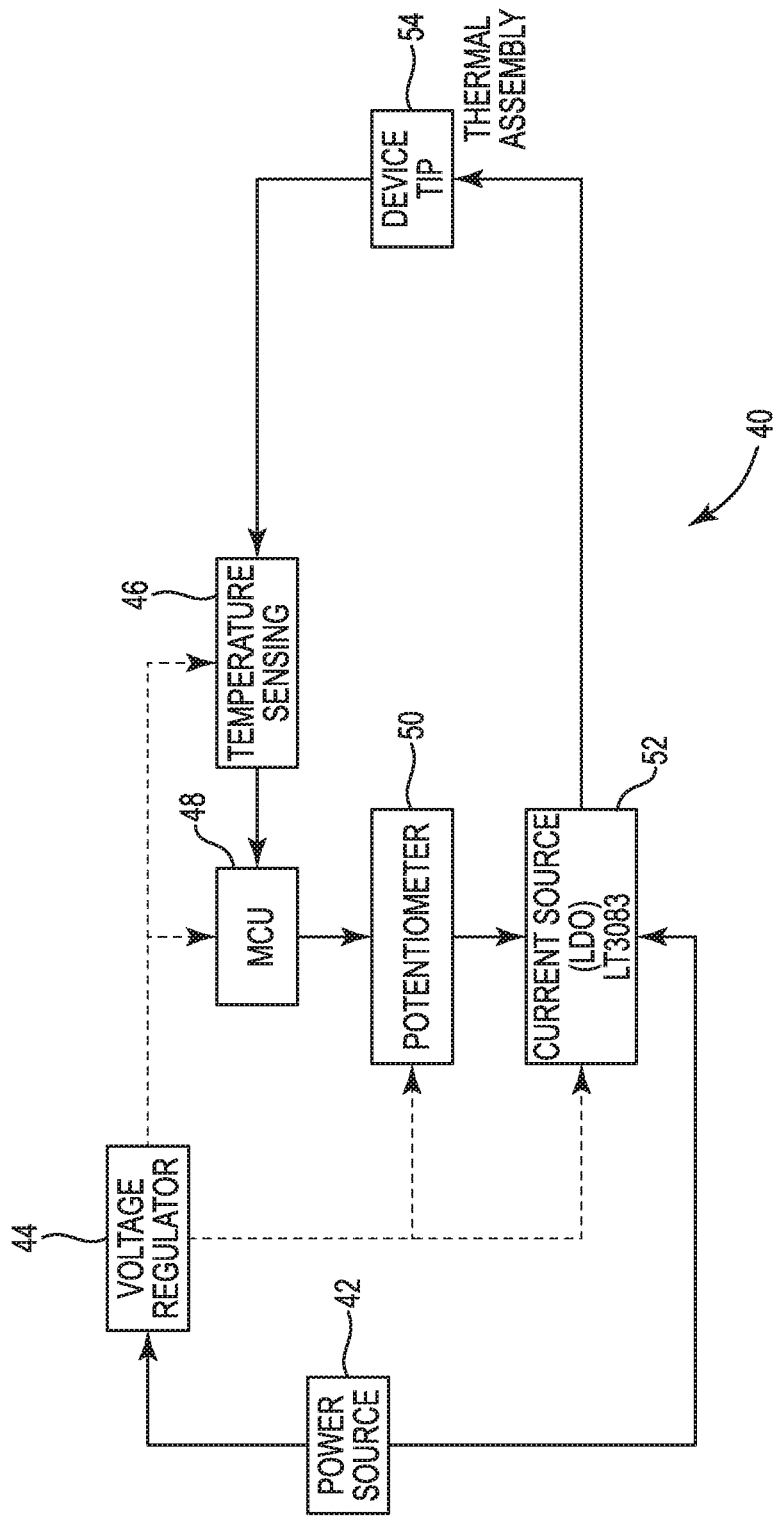
FIG. 2 is a schematic view illustrating an example architecture of the surgical system of FIG. 1.

FIG. 2 illustrates an example system architecture 40, which can correspond with the surgical system 10. System architecture 40 includes a power source 42 operably coupled to a voltage regulator 44. The voltage regulator 44 can be coupled to a temperature sensing module 46, a controller such as microcontroller unit 48, a potentiometer 50 and current source 52. The current source 52 receives a signal from the voltage regulator 44 and power source 42 to provide an electrical signal to a thermal assembly 54 including a heating element. In one example, the current source 52 can include a low-dropout, or LDO, regulator, which is a direct current (DC) linear voltage regulator that can regulate an output voltage even when a supply voltage is very close to the output voltage. The electrical signal heats the thermal assembly 54 to a preselected temperature or to a temperature within a selected temperature range. The temperature sensing module 46 detects the temperature of the thermal assembly 54 and provides the microcontroller unit 48 an output of representative of the detected temperature. The microcontroller unit 48 can monitor the temperature and selectively adjust the temperature of the thermal assembly 54 such as by adjusting the potentiometer 50 to control the current source 52.

Figure 3:
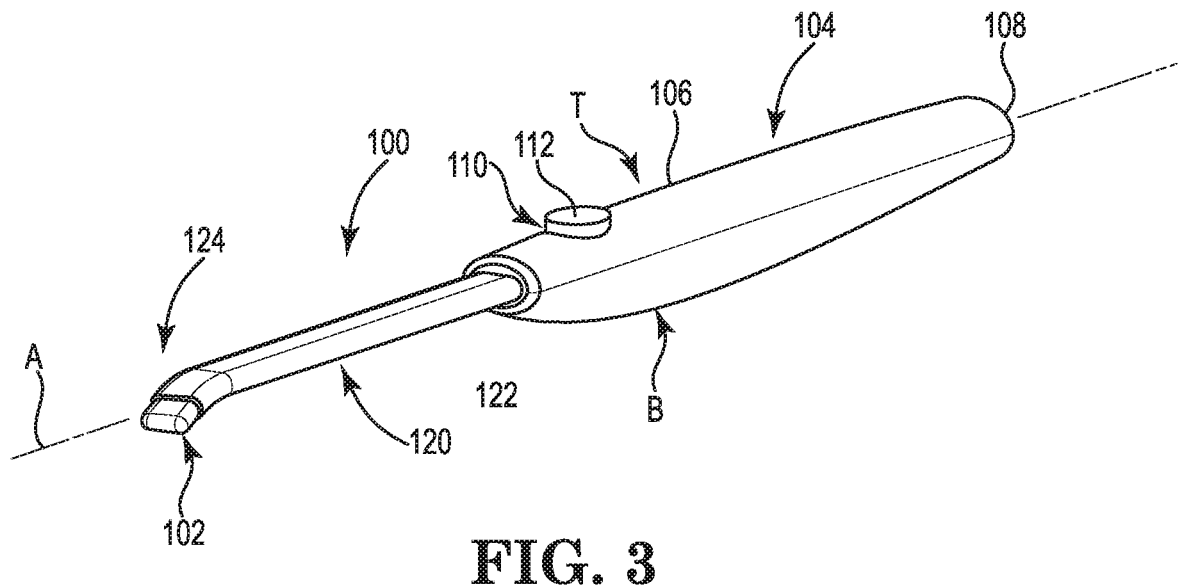
FIG. 3 is a perspective view illustrating an example of a surgical device of the system of FIG. 1 including a thermal assembly.

FIG. 3 illustrates an example of a surgical device 100 having thermal assembly 102 that can be used in conjunction with system 10. Thermal assembly 102 includes an exposed conductive surface configured to be electrically coupled to a source of electrical energy supplied from a power source that is not necessarily in the RF range. Thermal assembly 102 can be configured to provide for a robust electrode/tissue interface. The thermal assembly 102 may be formed to optimize hemostatic sealing of bone and tissue or coagulation without fluid, in conjunction with selected delivery of fluid, or for a particular application or anatomical geometry, or to perform other functions such as blunt dissection.

Another example of a surgical device can include a thermal assembly mounted on jaws or clamps that are movable with respect to each other. For example, jaws or clamps can selectively pinch tissue with a thermal assembly. Other examples are contemplated.

Surgical device 100 extending along longitudinal axis A includes a handpiece 104. Handpiece 104 includes a handle 106 that can include a finger grip portion with ridges (not shown) on the lower surface or bottom B of the device 100 and intended to be held in the surgeon's hand. In the illustrated example, the device 100 is cordless and includes the features of a thermal control system within the handpiece 104. The handpiece 104 includes a proximal end 108 for balance and, in one example, can include an electrical connector for electrically coupling a cable to the device 100 to supply power. Handpiece 104 may be configured to enable a user of device 100 to hold and manipulate device 100 between the thumb and index finger like a writing instrument or an electrosurgical pen. Handpiece 104 may comprise a sterilizable, rigid, electrically insulative material, such as a synthetic polymer (e.g., polycarbonate, acrylonitrile-butadiene-styrene).

The handle 106 can include an upper surface, or top T, that is opposite bottom B. A controller 110, such as a set of one or more switches 112 coupled to circuitry such as on a printed circuit board, in the example is disposed on top T and configured to be operated by the user's thumb or index finger to control one or more functions of the device 100. In the example, the switch can provide binary activation (on/off) control for each function and can be configured as a pushbutton. For example, switch 112 can be pushed to activate the thermal assembly 102 and released to deactivate the thermal assembly 102. Another switch (not shown) can be used selectively activate fluid dispersal. Other functions of the device are contemplated.

The surgical device 100 can include a probe assembly 120 extending distally from the handpiece 104. The probe assembly 120 in the example includes a shaft 122. The shaft 122, or other portions of device 100 may include one or more elements forming a subassembly to be generally one or more of rigid, bendable, fixed-length, variable-length (including telescoping or having an axially-extendable or axially-retractable length) or other configuration.

In one example, the handle 106 and shaft 122 can be formed from an electrically or thermally insulative material such as a high temperature micromolded polymer. Example insulative materials can include polytetrafluoroethylene (PTFE), polycarbonate (PC), polyoxymethylene (POM or acetal), or polyether ether ketone (PEEK).

The shaft 122 is configured to communicate a source of thermal energy to the thermal assembly 102. The shaft 122 carries one or more electrical conductors to a distal end 124 including the thermal assembly 102. Electrical pathways of the handpiece 104 and probe assembly 120 can be formed as conductive arms, wires, traces, other conductive elements, and other electrical pathways formed from electrically conductive material such as metal and may comprise stainless steel, titanium, gold, silver, platinum or any other suitable material.

In examples of the device 100 that can selectively disperse fluid, the shaft 122 includes a fluid lumen extending into the handpiece 104 for fluidly coupling to delivery tubing in a cable extending from proximal end 108. The fluid lumen includes can an outlet port disposed on or proximate the thermal assembly 102 for selectively dispersing fluid in the surgical site. In one example, fluid lumen can be included in a hypotube configured to mate with delivery tubing to supply fluid to thermal assembly 102. Hypotube can be constructed from non-conductive commonly used flexible tubing, such as polyvinyl chloride (PVC), PEEK, or a thermoplastic elastomer (TPE). In one example, the TPE is a polyether block amide (PEBA) available under the trade designation PEBAX from Arkema of Colombes, France.

Figure 4:
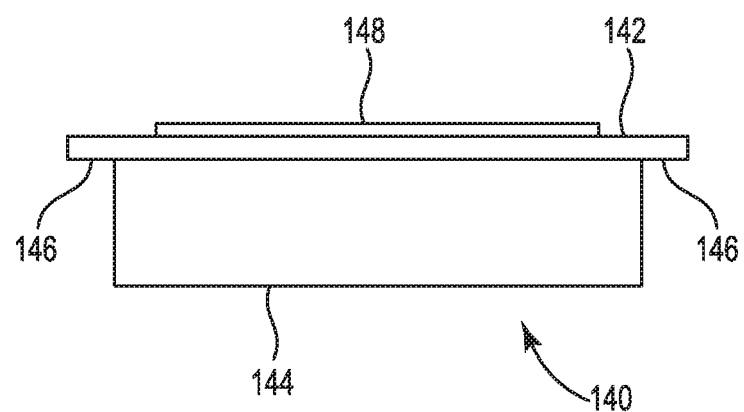
FIG. 4 is a schematic view illustrating example features of the thermal assembly of the surgical device of FIG. 3.

FIG. 4 illustrates an example thermal assembly 140, which can correspond with thermal assembly 102. Thermal assembly 140 includes a heating element 142 disposed on a substrate 144. The heating element 142 can include a set of tabs 146 that are configured to be communicatively coupled to a source of thermal energy. The thermal energy can be passed through the heating element 142 between the tabs 146. Various configurations and shapes of the thermal assembly 140 are contemplated, and this disclosure includes some examples of the configurations and shapes.

In one example, the source of thermal energy is an electrical current. The heating element 142 is formed of an electrically resistive material. The tabs 146 are couplable to electrical conductors in the shaft 122 and in electrical communication with the heating element 142. The electrical current is passed through the heating element 142 between the tabs 146 to heat the thermal assembly 140. In this example, electrically resistive material has a low thermal mass, or heat capacity, and can change temperature quickly depending on whether a current is applied. Additionally, the electrically resistive material can change resistance or impedance based on its temperature. In one example, the temperature of the heating element 142 can be monitored inferentially by detecting resistance or impedance of the heating element 142.

In one example, the heating element 142 is constructed from a material, such as an alloy, having a high resistivity. An example of an alloy having a high resistivity includes a nickel chrome, or nichrome, alloy. Other examples are contemplated. In one example, the heating element 142 is configured as a plating on the substrate 144. In other examples, the heating element 142 can be configured as a wire. An example thickness of a nichrome plating may be in a range of 0.001 to 0.005 inches. Other features of the heating element besides resistivity can include temperature coefficient of resistivity and corrosion resistance.

The substrate 144 in the example can be selected as having high thermal insulative properties as well as electrically insulative properties and durability. Examples of substrate 144 can include ceramics, glass, and plastics that are suitable for receiving a plating of resistive material. The substrate can be configured in a shape that is suited for the particular application of the surgical device 100. In some examples of a surgical device 100 in which fluid is selectively provided to the surgical site, the substrate may include an outlet port in fluid communication with the fluid lumen to disperse fluid from the heating assembly 102.

Portions of the thermal assembly 140 that interface with tissue are made smooth to improve lubricity so the thermal assembly 140 may slide along tissue without sticking. In one example, the surface of the thermal assembly 140 can include a lubricious coating 148 such as PTFE to further improve lubricity. The thermal assembly 140 is configured to slide smoothly along tissue without the use of saline.

Figure 5A:
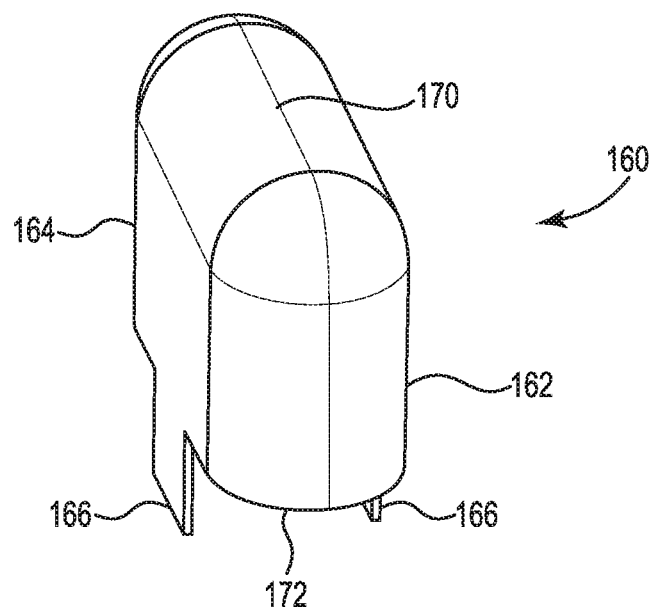
FIGS. 5A and 5B are perspective views of an example heating assembly suitable for use with surgical device of FIG. 3.
Figure 5B:
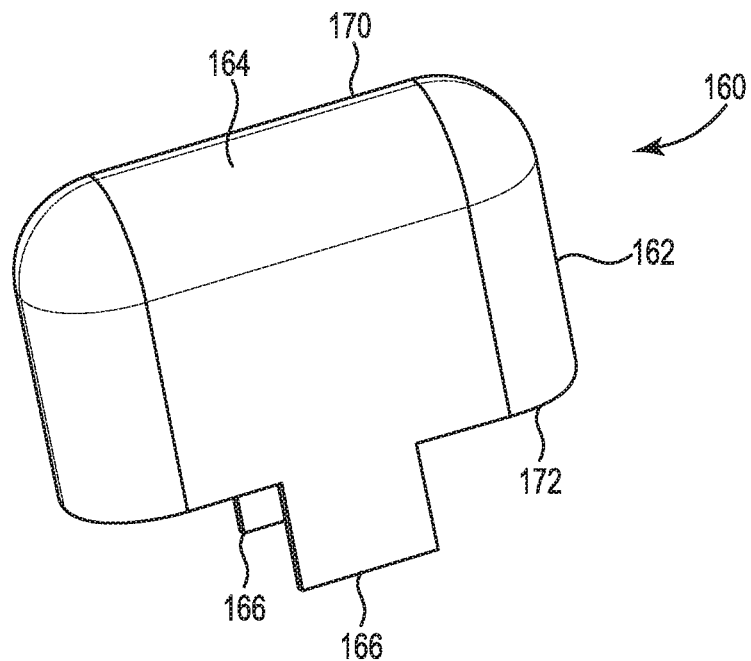

FIGS. 5A and 5B illustrate an example of a thermal assembly 160 that can correspond with thermal assemblies 140 and 102. The thermal assembly 160 includes a general shape of a blunted rectangular prism having a distal tip 170 and a proximal end 172. The thermal assembly 160 includes a blunted substrate 162 formed from a thermally insulative, electrically insulative, and durable material such as a ceramic, glass, plastic, or other material. A heating element 164 is plated over the distal tip 170 of the substrate 162 and can be made of a resistive material such as thin nichrome. The heating element 164 can be electrically coupled to an electrical signal, such as a current source, via tabs 166 on opposite sides of the substrate 162 proximate the proximal end 172.

Figure 6A:
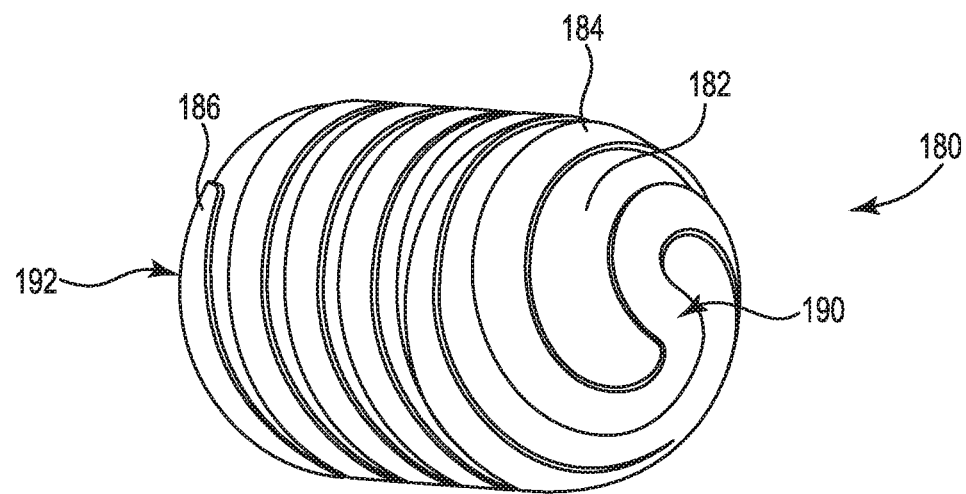
FIGS. 6A and 6B are perspective views of another example heating assembly suitable for use with surgical device of FIG. 3.
Figure 6B:
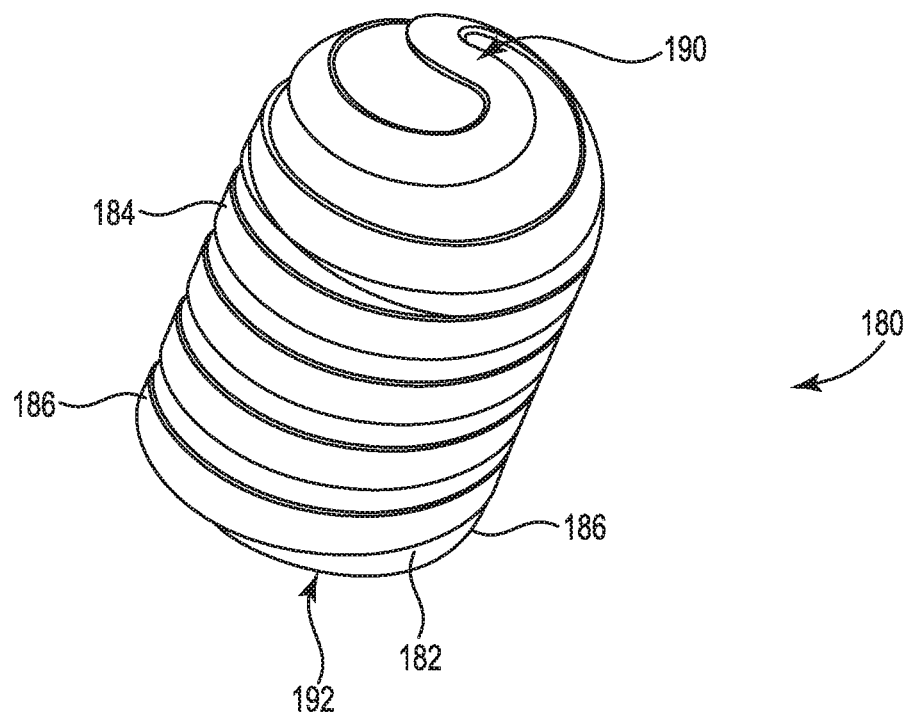

FIGS. 6A and 6B illustrate another example of a thermal assembly 180 that can correspond with thermal assemblies 140 and 102. The thermal assembly 180 includes a general shape of a blunted ogive or paraboloid having a distal tip 190 and a generally circular proximal end 192. The thermal assembly 180 includes a blunted substrate 182 formed from a thermally insulative, electrically insulative, and durable material such as a ceramic, glass, plastic, or other material. A heating element 184 is plated as a single electrical path configured as double helical trace over the distal tip 190 of the substrate 182 and can be made of a resistive material such as thin nichrome. The heating element 184 can be electrically coupled to an electrical signal, such as a current source, via tabs 186 on opposite sides of the substrate 182 proximate the proximal end 192. The tabs 186 in the example generally correspond with ends of the helical trace.

In one example, thermal assemblies 160, 180 can be attached to a shaft, such as shaft 122, and heating elements 164, 184 can be electrically coupled to electrical pathways within the shaft 122. Thermal assemblies 160, 180 can include lubricious coatings (not shown) such as PTFE over the heating elements 164, 184 to improve lubricity. Lubricious coatings may also cover the substrates 162, 182.

Although the present disclosure has been described with reference to preferred embodiments, workers skilled in the art will recognize that changes can be made in form and detail without departing from the spirit and scope of the present disclosure.

What is claimed is:

1. A surgical device, comprising:
a cordless handpiece having a handle, a rigid shaft, and a fluidless thermal assembly including a heating element and an electrically insulative and thermally insulative substrate, the thermal assembly comprising a blunted rectangular prism having a top generally planar face and an opposing bottom generally planar face, the handle including a switch;
the rigid shaft extending axially and distally from the handle, the shaft including a distal end; and
the thermal assembly operably coupled to the distal end of the shaft via a first tab projecting proximally from the top face, and a second tab projecting proximally from the bottom face, wherein the first and second tabs are couplable to electrical conductors within the shaft such that electrical current is passed through the heating element between the first and second tabs to heat the thermal assembly,
wherein the substrate provides a smooth and blunted shape along a length of the thermal assembly and the heating element includes an electrically resistive material electrically coupled to the switch and plated as a smooth plating surface extending from the width of the substrate, the resistive material is 0.001 to 0.005 inches thick on the substrate, the surgical device not including a fluid outlet port such that the thermal assembly is configured to provide hemostatic sealing of bone or tissue without application of fluid.

2. The surgical device of claim 1 including a controller to monitor and adjust temperature of the thermal assembly.

3. The surgical device of claim 2 wherein the heating element provides a temperature in a temperature range of 80 degree Celsius and 110 degrees Celsius when activated.

4. The surgical device of claim 1 wherein the resistive material is a nickel chrome alloy.

5. The surgical device of claim 1 wherein the thermal insulator is ceramic.

6. The surgical device of claim 1 wherein the thermal assembly includes a lubricious coating.

7. The surgical device of claim 6 wherein the lubricious coating includes PTFE.

8. The surgical device of claim 1, wherein the thermal assembly extends axially and distally from the shaft.

9. The surgical device of claim 1, wherein the set of tabs are included on opposite sides of the substrate.

10. The surgical device of claim 1, wherein the set of tabs are included with the heating element.

11. A hemostatic sealer, comprising:
a cordless handpiece having a source of energy, a handle, and a thermal assembly including:
an electrically insulative and thermally insulative smooth and blunted substrate, and
an electrically resistive material plated as a smooth exposed plating surface along a length of the substrate,
the thermal assembly comprising a blunted rectangular prism having a top generally planar face and an opposing bottom generally planar face;
the handle having a binary activation switch to activate the source of energy, the handle configured to be held in a user's hand and operated to control one function of the hemostatic sealer
a rigid shaft extending axially and distally from the handle, the shaft including a distal end; and
the thermal assembly coupled to the distal end of the rigid shaft via a first tab projecting proximally from the top face, and a second tab projecting proximally from the bottom face, wherein the first and second tabs are couplable to electrical conductors within the rigid shaft such that electrical current is passed through the resistive material between the first and second tabs to heat the thermal assembly, the thermal assembly having a length from the distal end, the substrate having a width, the resistive material operably extending from the width of the substrate and coupled to the switch to receive energy from the source of energy, the hemostatic sealer not including a fluid outlet port such that the thermal assembly is configured to provide hemostatic sealing of bone or tissue without application of fluid.

12. The hemostatic sealer of claim 11 wherein the source of energy is included in the handle.

13. The hemostatic sealer of claim 11, wherein the thermal assembly extends axially and distally from the shaft.

14. The hemostatic sealer of claim 11, wherein the set of tabs are included on opposite sides of the substrate.

15. The hemostatic sealer of claim 11, wherein the set of tabs are included with the resistive material.

* * * * *